US012311356B2

(12) United States Patent
Watano

(10) Patent No.: US 12,311,356 B2
(45) Date of Patent: May 27, 2025

(54) BIOLOGICAL SPECIMEN SEPARATION INSTRUMENT

(71) Applicant: FUJIFILM Corporation, Tokyo (JP)

(72) Inventor: Hirotaka Watano, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 895 days.

(21) Appl. No.: 17/462,218

(22) Filed: Aug. 31, 2021

(65) Prior Publication Data
US 2021/0394173 A1 Dec. 23, 2021

Related U.S. Application Data

(63) Continuation of application No. PCT/JP2020/012830, filed on Mar. 24, 2020.

(30) Foreign Application Priority Data

Mar. 25, 2019 (JP) ................................. 2019-056590

(51) Int. Cl.
  *B01L 3/00* (2006.01)
  *G01N 1/40* (2006.01)
(52) U.S. Cl.
  CPC ............ *B01L 3/502* (2013.01); *G01N 1/4077* (2013.01); *B01L 2200/026* (2013.01);
  (Continued)
(58) Field of Classification Search
  CPC ............... B01L 3/502; B01L 2200/026; B01L 2200/0689; B01L 2300/0681;
  (Continued)

(56) References Cited

U.S. PATENT DOCUMENTS

| 4,487,696 A | 12/1984 | Ferrara |
| 2003/0175167 A1 | 9/2003 | Takanori et al. |

(Continued)

FOREIGN PATENT DOCUMENTS

| JP | 5-52841 A | 3/1993 |
| JP | 8-201380 A | 8/1996 |

(Continued)

OTHER PUBLICATIONS

Wikipedia "Contact Angle" (https://en.wikipedia.org/wiki/Contact_angle) (Year: 2018).*

(Continued)

*Primary Examiner* — Jill A Warden
*Assistant Examiner* — Michael Stanley Gzybowski
(74) *Attorney, Agent, or Firm* — Birch, Stewart, Kolasch & Birch, LLP

(57) ABSTRACT

There is provided a biological specimen separation instrument with which a biological specimen can be stably separated into a predetermined component. The biological specimen separation instrument includes an accommodation instrument (1) that accommodates a collected biological specimen, a filter (128) for filtering a predetermined component in the biological specimen, and a holding instrument (100) that accommodates the filtered predetermined component, where the holding instrument is configured to be inserted into the accommodation instrument (1), a sealing member (130) is provided in an outer circumference of the holding instrument (100) on the tip side in the direction of insertion to to be movable in the accommodation instrument (1), in a state of being in liquid-tight contact with an interior wall of the accommodation instrument (1), the filter (128) is held to the holding instrument (100) by a holder (140) forming a biological specimen inflow port (142) to the filter (128), and in a case where the filter (128) and the holding (Continued)

instrument (100) are cross-sectionally viewed, the sealing member (128) is positioned on a side opposite to the direction of insertion from an imaginary line (148) from an end part of the filter (128), where the imaginary line (148) is in contact with a tip side end part (146A) on an opposite side across a center of the filter (128).

11 Claims, 12 Drawing Sheets

(52) U.S. Cl.
CPC .................. *B01L 2200/0689* (2013.01); *B01L 2300/0681* (2013.01); *B01L 2300/12* (2013.01); *B01L 2300/161* (2013.01); *G01N 2001/4088* (2013.01)

(58) Field of Classification Search
CPC ........... B01L 2300/12; B01L 2300/161; G01N 1/4077; G01N 2001/4088
See application file for complete search history.

(56) References Cited

U.S. PATENT DOCUMENTS

| | | |
|---|---|---|
| 2008/0300397 A1 | 12/2008 | Kenrick et al. |
| 2011/0008908 A1 | 1/2011 | Biesbrouck |
| 2014/0042094 A1 | 2/2014 | Montagu et al. |
| 2015/0153323 A1 | 6/2015 | Huemer |
| 2015/0231536 A1 | 8/2015 | Nogami et al. |
| 2016/0355436 A1 | 12/2016 | Chen et al. |
| 2018/0304287 A1 | 10/2018 | Meuler et al. |

FOREIGN PATENT DOCUMENTS

| | | |
|---|---|---|
| JP | 2003-270239 A | 9/2003 |
| JP | 2007-536 A | 1/2007 |
| JP | 2007-3479 A | 1/2007 |
| JP | 2007-6973 A | 1/2007 |
| JP | 2010-518393 A | 5/2010 |
| JP | 2012-18514 A | 1/2012 |
| JP | 2015-528328 A | 9/2015 |
| JP | 2015-530566 A | 10/2015 |
| WO | WO 2014/064921 A1 | 5/2014 |
| WO | WO 2019/025914 A1 | 2/2019 |

OTHER PUBLICATIONS

Wikipedia "Silicon Rubber" (https://en.wikipedia.org/wiki/Silicone_rubber) (Year: 2019).*
International Preliminary Report on Patentability and Written Opinion of the International Searching Authority (Forms PCT/IB/373 and PCT/ISA/237) for International Application No. PCT/JP2020/012829, dated Sep. 28, 2021, with an English translation.
International Search Report (Form PCT/ISA/210) for International Application No. PCT/JP2020/012829, dated Jun. 9, 2020, with an English translation.
International Preliminary Report on Patentability and Written Opinion of the International Searching Authority (Forms PCT/IB/373, and PCT/ISA/237) for International Application No. PCT/JP2020/012830, dated Sep. 28, 2021, with an English translation.
International Search Report (Form PCT/ISA/210) for International Application No. PCT/JP2020/012830, dated Jun. 9, 2020, with an English translation.
U.S. Office Action for U.S. Appl. No. 17/462,989, dated May 30, 2024.
U.S. Appl. No. 17/462,989, filed Aug. 31, 2021.

* cited by examiner

BIOLOGICAL SPECIMEN SEPARATION INSTRUMENT

CROSS-REFERENCE TO RELATED APPLICATIONS

The present application is a Continuation of PCT International Application No. PCT/JP2020/012830 filed on Mar. 24, 2020 claiming priority under 35 U.S.C § 119(a) to Japanese Patent Application No. 2019-056590 filed on Mar. 25, 2019. Each of the above applications is hereby expressly incorporated by reference, in its entirety, into the present application.

BACKGROUND OF THE INVENTION

1. Field of the Invention

The present invention relates to a biological specimen separation instrument and particularly relates to a biological specimen separation instrument in which a collected biological specimen is filtered with a separation membrane.

2. Description of the Related Art

As a method of collecting a biological specimen for collecting and examining a biological specimen, for example, in the case of blood, there are a general blood collection in which a certain qualified person such as a doctor collects blood from a vein using a syringe and a self-blood collection in which an examination subject inserts a blood collection needle into a finger of the hand of the examination subject to collect blood.

The blood collected by the general blood collection is transported to a medical institution or an examination institution in a state of being sealed in a collection container, and the examination is carried out there. In a case where the blood sample is transported without being separated into blood cells and plasma or serum, the examination is carried out after the blood sample is separated into blood cells and plasma or serum by a centrifuge at the medical institution or the examination institution. In the self-blood collection carried out by an examination subject, the blood sample after the blood collection is separated into blood cells and plasma or serum by a separation membrane and, in the state of being separated, transported to an examination site where the examination is carried out.

In a case where self-blood collection is carried out, the blood separation is carried out using a separation instrument. For example, JP1993-52841A (JP-H5-52841A) discloses a blood separation method in which a blood separation member having a filtration unit is inserted into a blood collection tube, the blood separation member is moved downward, and the blood separation member is moved to a boundary between serum and blood clot. JP2012-18514A discloses a blood separation cylinder in which a valve case having a check valve for segregating blood cells and cell components which are separated by a blood separation membrane from plasma or serum is provided at the tip of the separation cylinder body, and a blood separation membrane gasket is attached to the main body of the separation cylinder.

In addition, JP2003-270239A discloses a biological specimen separation instrument that includes a biological specimen collection unit that accommodates a collected biological specimen, a filtering unit for causing a predetermined component in the collected biological specimen to pass, and a separated component accommodation unit that accommodates the predetermined component that has passed through the filtering unit.

SUMMARY OF THE INVENTION

For separating blood using a filter, it is necessary to prevent the hydrophobization of the filter. In a case where a gasket that is used for maintaining the smoothness and liquid tightness between containers that are used in a case where separating blood is formed of silicone rubber, there has been a case where the filter is hydrophobized due to the influence of the siloxane generated from the silicone rubber. In a case where the filter was hydrophobized, blood cells did not enter the central part of the filter, and the blood cells intruded between the filter and the holding part that holds the filter, whereby the blood cells were destroyed by the filter, that is, hemolysis occurred. The separation instruments disclosed in JP1993-52841A (JP-H5-52841A), JP2012-18514A, and JP2003-270239A have configurations in which a filter is held by being in direct contact with a gasket, or no other member is interposed between the filter and the gasket. As a result, there is a concern that the filter is hydrophobized due to the siloxane generated from the gasket.

The present invention has been made in consideration of such circumstances, and an object of the present invention is to provide a biological specimen separation instrument in which the hydrophobization of a filter for separating a biological specimen can be prevented and with which a biological specimen can be separated.

For achieving the object of the present invention, a biological specimen separation instrument according to an aspect the present invention includes a first container that accommodates a collected biological specimen, a filter for filtering a predetermined component in the collected biological specimen, and a second container that accommodates the predetermined component filtered by the filter, the second container being configured to be inserted into the first container, where a sealing member is provided in an outer circumference of the second container on the tip side in the direction of insertion into the first container to to be movable in the first container, in a state of being in liquid-tight contact with an interior wall of the first container, in which the filter is held in the second container by an intermediate member which is provided between the filter and the sealing member and which forms an biological specimen inflow port to the filter, and in a cross-sectional view in which the filter and the second container are cut along the direction of insertion, the sealing member is positioned on a side opposite to the direction of insertion from an imaginary line drawn from an end part of the filter in contact with the biological specimen inflow port to be in contact with a tip side end part of the biological specimen inflow port on an opposite side across a center of the filter.

According to the biological specimen separation instrument according to the aspect of the present invention, since the filter is held by the intermediate member, the filter can be prevented from coming into contact with the sealing member, and the filter can be prevented from being hydrophobized due to siloxane. Further, the position of the sealing member is arranged on the side opposite to the direction of insertion of the second container from the imaginary line with which the filter and the tip side end part of the biological specimen inflow port are in contact. This makes it possible for the intermediate member to be interposed between the sealing member and the filter, and thus the siloxane generated from the sealing member can be prevented from being reaching the filter. As a result, the filter can be prevented from being hydrophobized.

DESCRIPTION OF THE PREFERRED EMBODIMENTS

Hereinafter, a biological specimen separation instrument according to an embodiment of the present invention will be described with reference to the attached drawings. In the present invention, the numerical value range indicated by using "to" means a range including the numerical values before and after "to" as the lower limit value and the upper limit value, respectively.

[Biological Specimen Separation Instrument]

Figure 1:
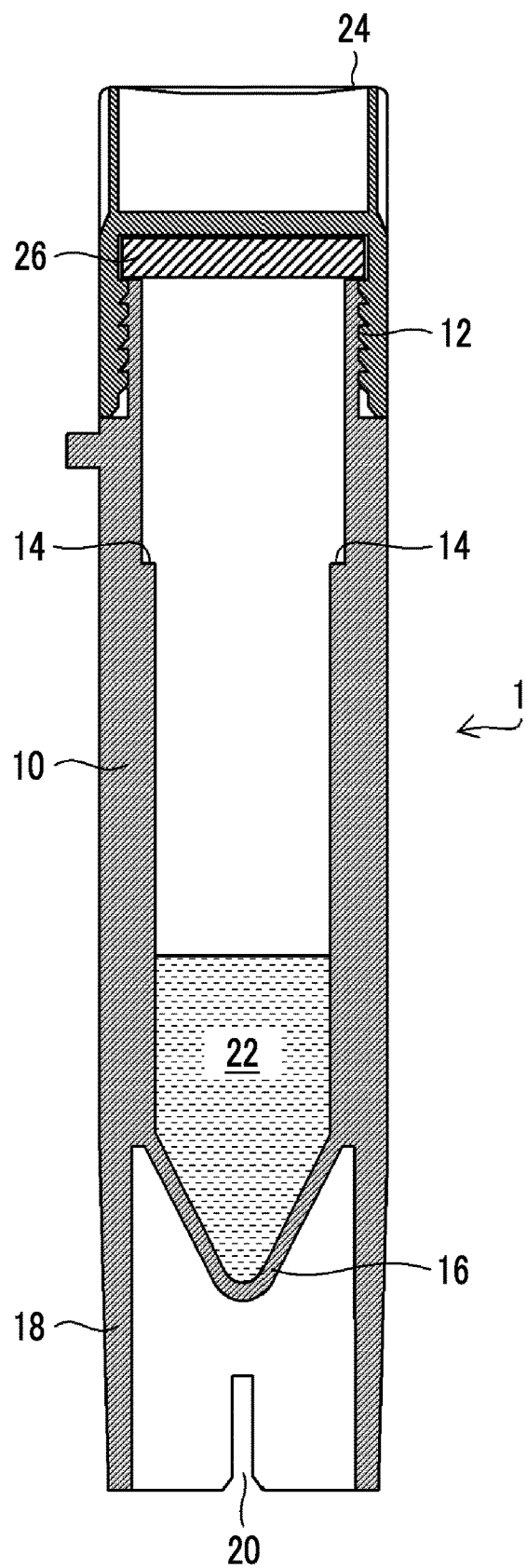
FIG. 1 is a cross-sectional view illustrating an example of a configuration of an accommodation instrument.
Figure 2:
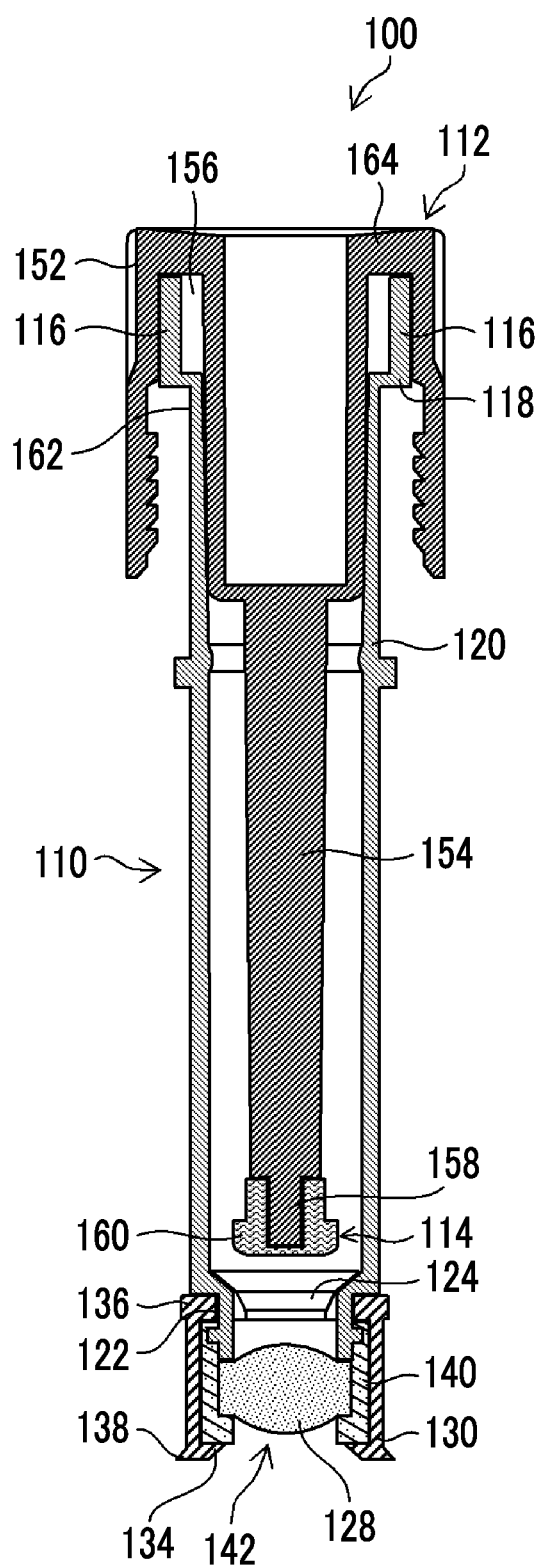
FIG. 2 is a cross-sectional view illustrating an example of a configuration of a holding instrument having a filter.
Figure 3:
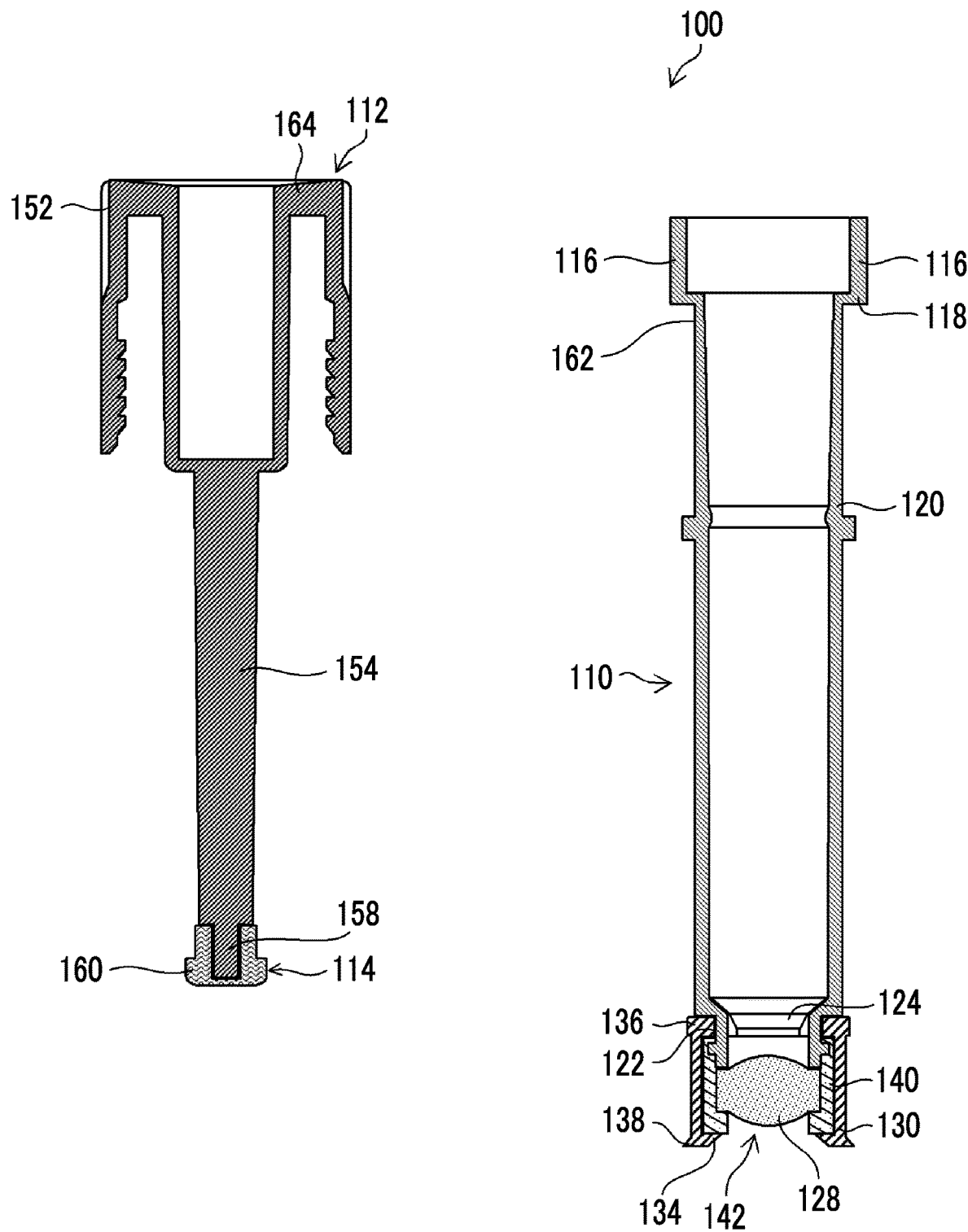
FIG. 3 is a disassembled cross-sectional view of the holding instrument disassembled into a cylinder and a cap.
Figure 4:
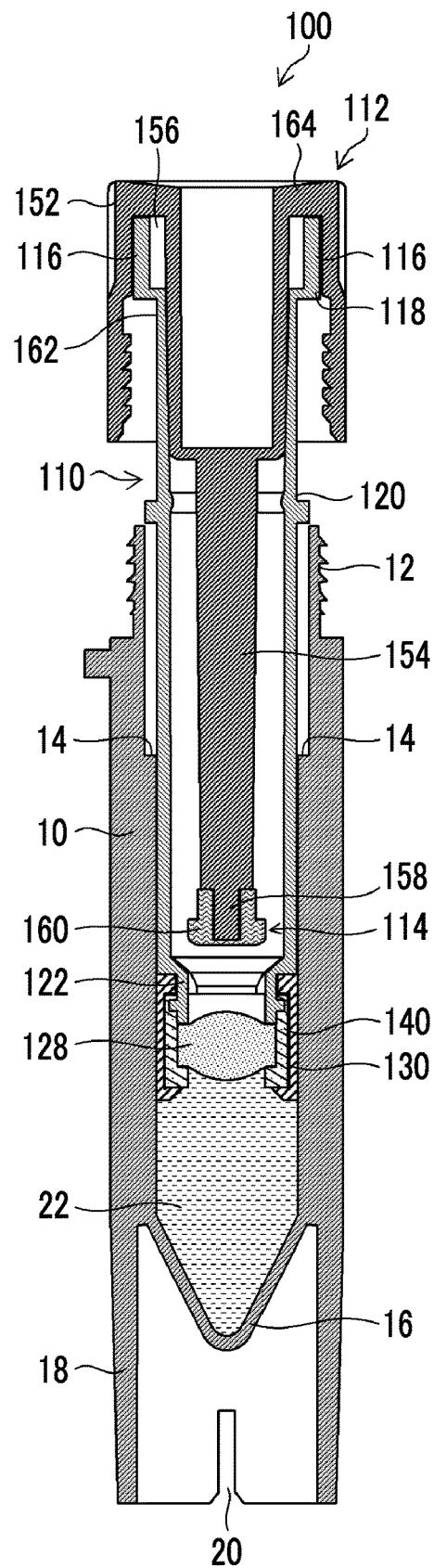
FIG. 4 is a view for explaining a state where the holding instrument is inserted into the accommodation instrument.
Figure 5:
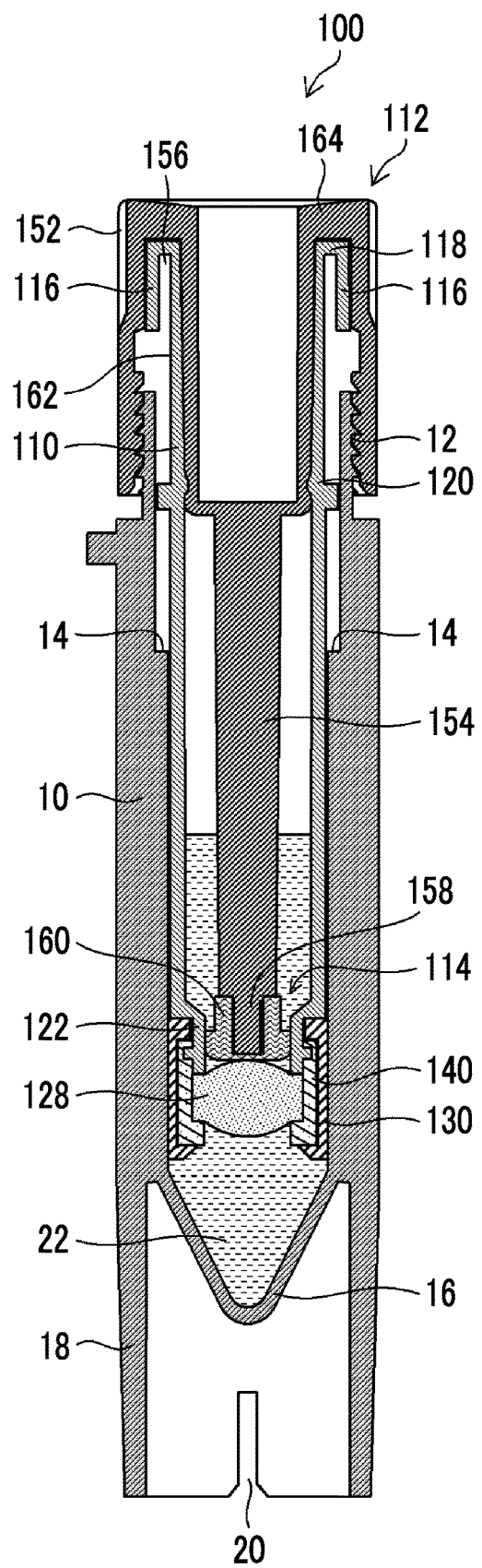
FIG. 5 is a view for explaining a state after separating a biological specimen using a separation instrument.
Figure 6:
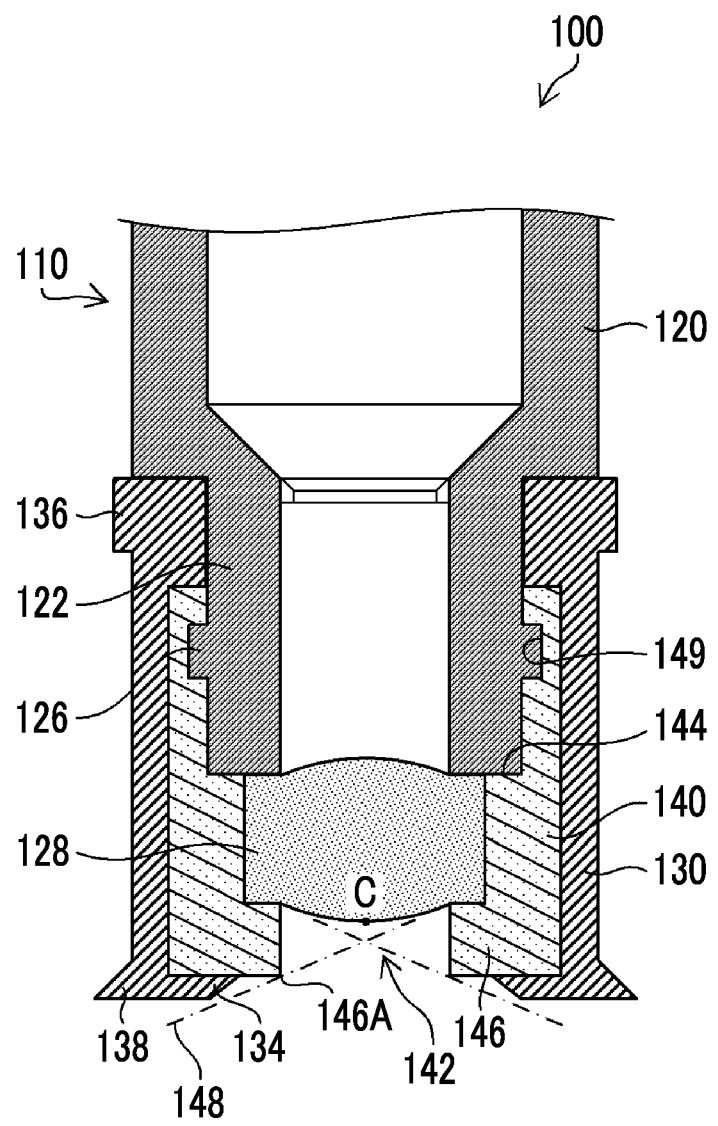
FIG. 6 is an enlarged view of a tip part of the holding instrument illustrated in FIG. 2.

The biological specimen separation instrument will be described with reference to FIG. 1 to FIG. 6. FIG. 1 is a cross-sectional view illustrating an example of a configuration of an accommodation instrument (a first container), and FIG. 2 is a cross-sectional view illustrating an example of a configuration of a holding instrument (a second container). FIG. 3 is a disassembled cross-sectional view of the holding instrument illustrated in FIG. 2, which is disassembled into a cylinder and a cap. FIG. 4 is a view for explaining a state where the holding instrument is inserted into the accommodation instrument, and FIG. 5 is a view for explaining a state where a biological specimen is separated by a separation instrument provided in the holding instrument. FIG. 6 is an enlarged view of a tip part of the holding instrument. In the following description, the description will be made using blood as an example of the biological specimen; however, the biological specimen of the present embodiment is not limited to blood and other biological specimens can also be used.

<<Accommodation Instrument (First Container)>>

As illustrated in FIG. 1, an accommodation instrument 1 has a cylindrical blood collection container 10 made of a transparent material. On the upper end side of the blood collection container 10, a screw part 12 is formed on the outer surface, and a locking part 14 is provided to protrude on the inner surface. In addition, a conical bottom part 16 protruding toward the lower end side is formed at the lower end part of the blood collection container 10. A cylindrical leg part 18 is formed around the bottom part 16. Here, the "upper" and the "lower" respectively mean "upper" and "lower" in a state where the leg part 18 is installed on the placement surface.

The leg part 18 has the same outer diameter as the sample cup (not illustrated in the drawing) that is used in the analysis and examination of the blood, and preferably, and it is preferable that a slit groove 20 is formed at a position where the leg parts face each other at the lower end thereof, in the vertical direction. Further, as illustrated in FIG. 1, the blood collection container 10 preferably accommodates a diluent 22 of a required amount, for example, 500 mm$^3$.

As illustrated in FIG. 1, in the accommodation instrument 1 before use, it is preferable that an upper end opening of the blood collection container 10 is sealed by a cap 24 through a packing 26. Further, in a case of collecting blood, it is preferable that the upper end opening is sealed by the cap 24 and the packing 26 after the cap 24 is removed and blood is collected.

For blood collection in the blood collection container 10, blood can be collected directly. In addition, a blood sample can be collected by absorbing blood into an absorbent material and putting the absorbent material into the blood collection container 10.

<<Holding Instrument (Second Container)>>

There is a possibility that a long time elapses until the carrying out of the analysis of the collected blood sample which is in a state of being diluted in the accommodation instrument 1. During this time, there is a possibility that in a case where hemolysis of red blood cells occurs, substances and enzymes that are present in the blood cells are eluted into plasma or serum, which affects the examination results, or the optical absorption of the eluted hemoglobin affects a case of a measurement in which an amount of an analysis target component is measured with optical information such as the optical absorption of the analysis target component. Accordingly, it is preferable to prevent hemolysis. For this reason, a predetermined component (a plasma component in the present embodiment) is separated from the diluted blood sample with a filter, and the separated plasma component is accommodated in the holding instrument. The filter is preferably provided in the holding instrument, and the plasma component that has passed through the filter is directly accommodated in the holding instrument. The filter can be used so that, for example, pressure is applied to a diluted blood sample to capture a blood cell component with the filter and the plasma component is allowed to pass to separate blood cells, whereby the plasma component is recovered. In this case, it is preferable to use an anticoagulant. Further, for ensuring the accuracy of the measurement, it is preferable that the plasma that has passed through the filter does not flow back to the blood cell side. Therefore, specifically, the backflow prevention unit disclosed in JP2003-270239A can be provided in the holding instrument.

FIG. 2 is a cross-sectional view illustrating an example of a configuration of a holding instrument 100 having a filter 128. The holding instrument 100 illustrated in FIG. 2 is composed by combining a cylinder 110 and a cap 112. The cylinder 110 is configured to be inserted into the blood collection container 10 of the accommodation instrument 1. The cap 112 is screwable to the accommodation instrument 1, and a sealing member 114 that prevents the plasma in the cylinder 110 from flowing back into the blood collection container 10 is provided at the lower end of the cap 112.

The cylinder 110 is made of a transparent material and has a cylindrical shape. An expanded diameter part 116 is formed at an upper end part 162 of the cylinder 110. The expanded diameter part 116 is connected to a body part 120 through a thin-wall portion 118. As illustrated in FIG. 6, a reduced diameter part 122 is formed at the lower end part of the cylinder 110. A locking protrusion part 124 is formed on the inner surface of the reduced diameter part 122. Further, an outer flange part 126 is formed on the outside of the reduced diameter part 122. The filter 128 is provided on the lower end side of the reduced diameter part 122, that is, on the tip side in the direction of insertion into the accommodation instrument 1. The filter 128 is configured to allow the passage of the plasma in the blood and block the passage of the blood cells. A holder 140 is mounted on a part of the outside of the reduced diameter part 122 and the outside of the filter 128. In addition, a sealing member 130 is mounted on the outside of the holder 140. With the sealing member 130, the liquid tightness between the blood collection container 10 and the cylinder 110 in a case where the cylinder 110 is fitted into the blood collection container 10 can be held. Further, the smoothness between the blood collection container 10 and the cylinder 110 can be held. The holder 140 has a groove 149 on the inner surface thereof, and thus it is possible to prevent the holder 140 and the sealing member 130 from falling from the reduced diameter part 122 since the outer flange part 126 is fitted to the groove 149 and the sealing member 130 is mounted on the outside of the holder 140. The holder 140 makes the groove 149 fit to the outer flange part 126 and is held by the sealing member 130 in the vertical direction. A stepped part 144 is provided on the inner surface of the holder 140, and the tip of the reduced diameter part 122 is in contact with the stepped part 144. A protrusion part 146 protruding inward is provided on the lower end side of the holder 140. The filter 128 is held by being sandwiched, in the vertical direction, between the reduced diameter part 122 of the cylinder 110 and the protrusion part 146 of the holder 140. The inner opening formed by the protrusion part 146 of the holder 140 serves as an inflow port 142 (corresponding to the biological specimen inflow port) into which the blood flows from the blood collection container 10. In the sealing member 130, a second protrusion part 136 is provided in the outer circumference of the upper end part, and a third protrusion part 138 is provided in the outer circumference of the lower end part. The outer diameters of the second protrusion part 136 and the third protrusion part 138 of the sealing member 130 are larger than the outer diameter of the body part 120.

As the filter 128, it is preferable to use a hydrophilic filter since it is necessary to filter blood. Specifically, it is preferable to use a depth filter. Further, in FIG. 2, FIG. 3, and FIG. 6, although the description is made using the configuration in which one filter is used described, a configuration having two or more depth filters may be used.

The cap 112 is composed of a substantially cylindrical grip part 152 and a mandrel part 154 that is concentric with the grip part 152 and extends downward. A cylindrical space 156 to which the expanded diameter part 116 of the cylinder 110 is capable of fitting is formed in the inner upper end part of the grip part 152, and the lower portion thereof is screwed to be screwable to a screw. A lower end part 158 of the mandrel part 154 is formed in a pin shape, and the sealing member 114 is provided attachably and detachably in the lower end part 158. The sealing member 114 is made of silicone rubber. The lower end part of the sealing member 114 has a substantially columnar shape formed in an outer flange shape, and a stepped part 160 is formed around the outer circumference. The grip part 152 has an apex part 164, and the inner surface of the apex part 164 comes into contact with the expanded diameter part 116. The cylinder 110 and the cap 112 may not be combined until they are used, and may be used by being combined by a user in a case of being used. Alternatively, the cylinder 110 and the cap 112 may be combined from the beginning.

Next, a blood separation method after collecting blood will be described with reference to FIG. 4 and FIG. 5. First, the cap 24 is removed, and the cylinder 110 to which the cap 112 is attached is fitted into the blood collection container 10, where the blood collection container 10 have accommodated a diluted blood sample.

Next, as illustrated in FIG. 4, the grip part 152 is screwed to the screw part 12. First, the grip part 152 and the cylinder 110 rotate. When the locking part 14 of the blood collection container 10 is locked to a stopper part (not illustrated in the drawing) formed on the outer circumference surface of the cylinder 110, the rotation of the cylinder 110 is restricted, and the thin-wall portion 118 is ruptured by twisting. As a result, the cylinder 110 is separated into the body part 120 and the expanded diameter part 116. In a case where the grip part 152 is further rotated, the upper end part 162 of the body part 120 enters the space 156 inside the expanded diameter part 116. Since the cylinder 110 is pressed downward by the inner surface of the apex part 164 of the grip part 152, the cylinder 110 is further lowered.

As the cylinder 110 is lowered, the filter 128 held by the cylinder 110 moves to the bottom part 16 of the blood collection container 10. At that time, plasma moves to the side of the cylinder 110 through the filter 128, and blood cells cannot pass through the filter 128 and thus remain on the side of the blood collection container 10.

Since the outer diameters of the second protrusion part 136 and the third protrusion part 138 of the sealing member 130 are larger than the outer diameter of the body part 120 of the cylinder 110, the cylinder 110 is movable in a state of being in liquid-tight contact with the interior wall of the blood collection container 10. As a result, in the process of fitting the cylinder 110 into the blood collection container 10, there is no possibility that the blood or the diluent 22 in the blood collection container 10 leaks to the outside through the gap between the blood collection container 10 and the cylinder 110.

In a case where the grip part 152 is screwed to the screw part 12 up to the lowermost part, the sealing member 114 fits to the reduced diameter part 122. The flow channel between the blood collection container 10 and the cylinder 110 is sealed by the sealing member 114. The sealing member 114 prevents the mixing of the plasma and the blood cells due to backflow. As a result, the state of separation into blood cells and plasma or serum is reliably held.

[Positional Relationship Between Filter and Sealing Member]

In the present embodiment, the positions of the sealing member 130 and the filter 128 are specified in order to prevent the filter 128 from being hydrophobized by the siloxane generated from the sealing member 130. As illustrated in FIG. 6, the holder 140 (corresponding to the intermediate member) is arranged between the filter 128 and the sealing member 130 to prevent the filter 128 from coming into direct contact with the sealing member 130. Further, the sealing member 130 is arranged as follows in a cross-sectional view in which the filter 128 and the holding instrument 100 are cut along the direction of insertion into the accommodation instrument 1. An imaginary line 148 in contact with a tip side end part 146A of the inflow port 142, on a side opposite to a center C of a surface of an inflow port 142 side of the filter 128, is drawn from the end part of the filter 128 in contact with the inflow port 142. The sealing member 130 is positioned on the side opposite to the direction of insertion of the holding instrument 100, from this imaginary line 148. In FIG. 6, the sealing member 130 has a first protrusion part 134 protruding inward, and the holder 140 is held from the under side by the first protrusion part 134. The first protrusion part 134 is arranged on the side opposite to the direction of insertion, that is, on the upper side of the imaginary line 148. With such a configuration, the holder 140 can be interposed between the sealing member 130 and the filter 128. As a result, the siloxane generated from the sealing member 130 can be made to be difficult to reach the filter 128, and thus the filter can be prevented from becoming hydrophobized.

As the material of the sealing member 130, since the cylinder 110 is lowered in a state where the sealing member 130 is closely attached to the inner surface of the blood collection container 10 as described above, the sealing member 130 preferably has smoothness. In order to impart the smoothness to the sealing member 130, the Shore A hardness of the sealing member 130 is set to be, for softness, 20 or more and 90 or less. In a case where the Shore A hardness is set within the above range, both the liquid tightness and the smoothness can be achieved between the blood collection container 10 and the sealing member 130. Regarding the Shore A hardness, a numerical value measured according to JIS K 6253 can be used.

In addition, for suppressing the generation of siloxane, as the material of the sealing member 130, any material of fluororubber, isoprene rubber, butyl rubber, chlorinated butyl rubber, and a thermoplastic elastomer is preferably used. As the thermoplastic elastomer, any one of a polystyrene-based thermoplastic elastomer, a polyolefin-based thermoplastic elastomer, a vinyl chloride-based thermoplastic elastomer, a polyurethane-based thermoplastic elastomer, a polyester-based thermoplastic elastomer, a polyamide-based thermoplastic elastomer, or a polybutadiene-based thermoplastic elastomer can be used. In a case where the sealing member 130 is composed of the above-described material, it is possible to suppress or prevent the generation of siloxane from the sealing member 130.

The filter 128 is held by being pressed by the tip of the reduced diameter part 122 of the cylinder 110 and the protrusion part 146 of the holder 140 in the vertical direction and from the periphery by the holder 140. Due to being pressed in the vertical direction by the tip of the reduced diameter part 122 and the protrusion part 146 of the holder 140, the thickness of the central part of the filter 128 is thicker than that of the end part. That is, the end part of the filter 128 is held by being compressed and thinned. This can make it difficult for blood to pass through the end part of the filter 128 in a case of being filtered. As a result, blood can be filtered at the central part of the filter 128. In addition, since the intrusion in the end part direction can be suppressed, hemolysis can be prevented.

Due to coming into direct contact with the filter 128, the holder 140 is preferably formed of a material that does not generate siloxane. For this reason, as the material of the holder 140, it is preferable to use a resin, specifically, selected from polyvinyl chloride, polyethylene, polypropylene, polystyrene, acrylonitrile-butadiene-styrene, acrylonitrile-styrene, polymethylmethacrylate, polyethylene terephthalate, polyamide, polyacetal, polycarbonate, a polyphenyl ether, polybutylene terephthalate, and polyvinylidene fluoride.

Further, the contact angle of the holder 140 is preferably larger than the contact angle of the filter 128. In a case where the contact angle of the holder 140 is increased, it is possible to prevent the blood filtered by the filter 128 from passing through the holder 140 side, that is, passing between the filter 128 and the holder 140. This makes it possible to prevent hemolysis of the blood. The contact angle is preferably such that the contact angle of the filter 128 is 50° or less, and thus the contact angle of the holder 140 is preferably larger than the contact angle of the filter 128, more than 50°. The contact angle can be measured according to JIS R 3257.

Further, regarding the hardness, the holder 140 preferably has a Shore D hardness of 20 or more. The Shore D hardness can be measured according to JIS K 7215.

Figure 7:
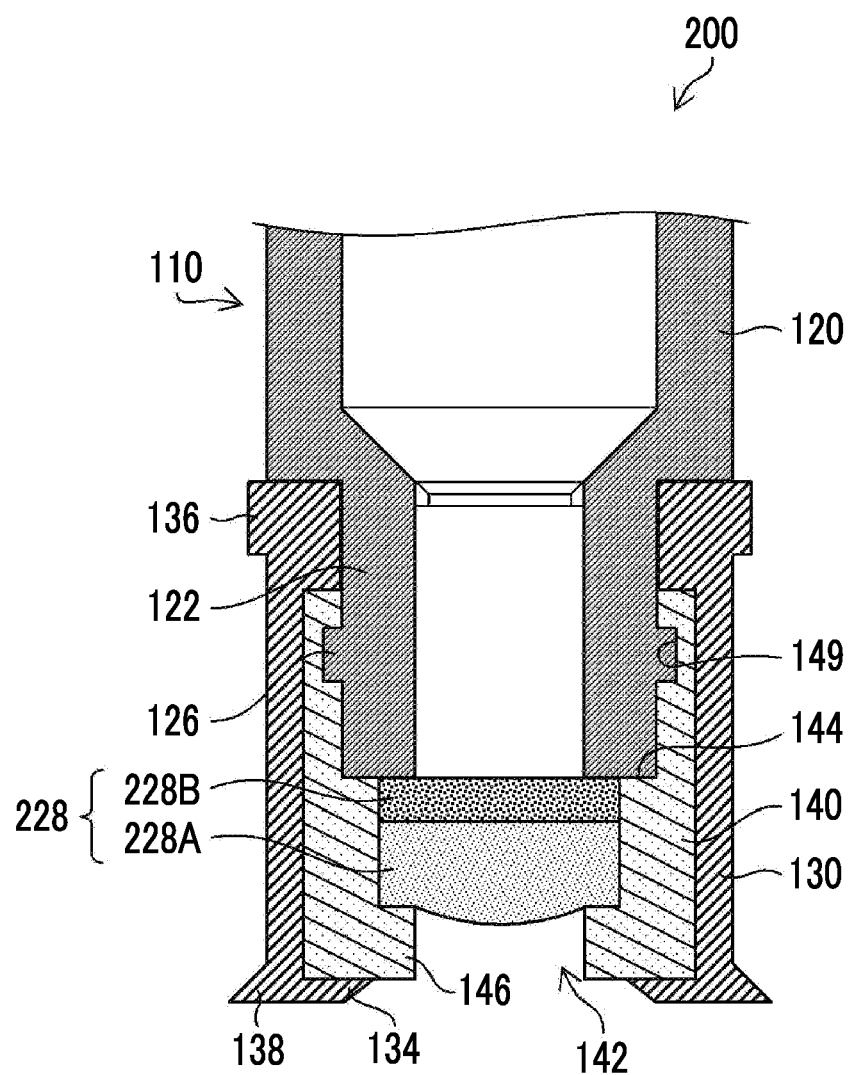
FIG. 7 is an enlarged view of another embodiment of the tip part of the holding instrument.
Figure 8:
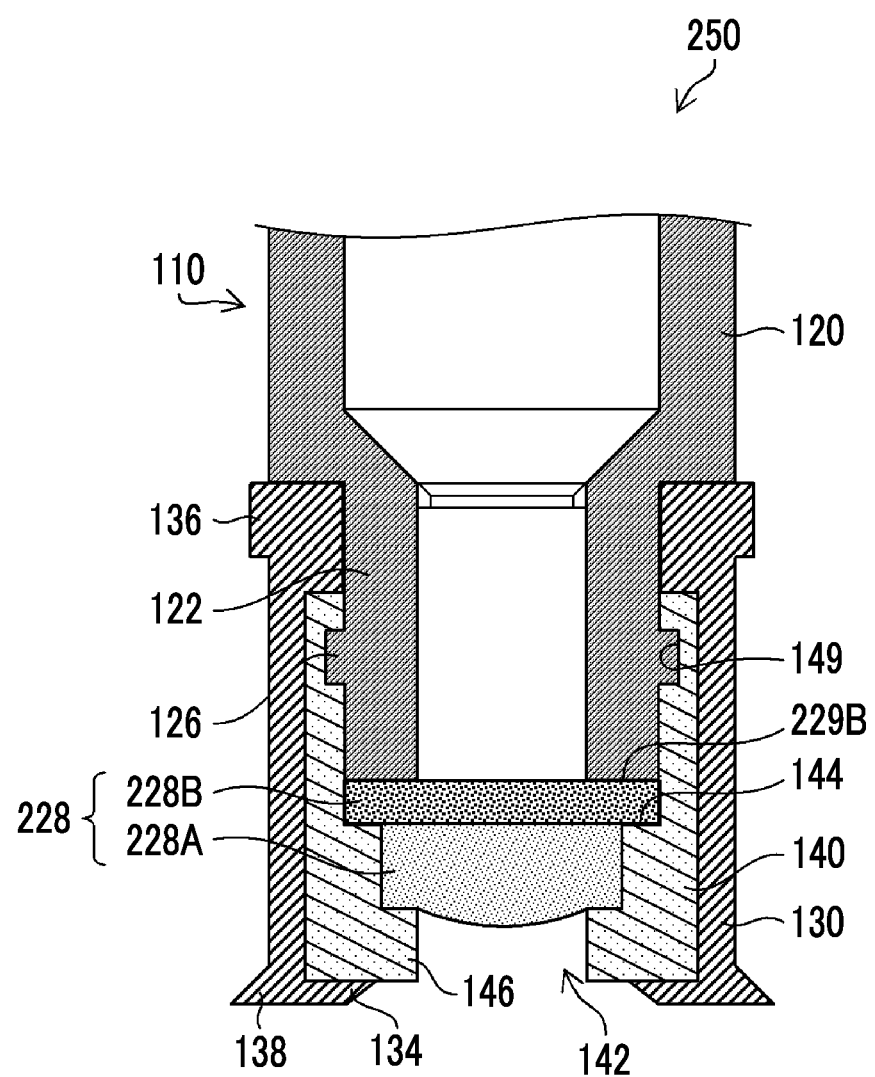
FIG. 8 is an enlarged view of still another embodiment of the tip part of the holding instrument.
Figure 9:
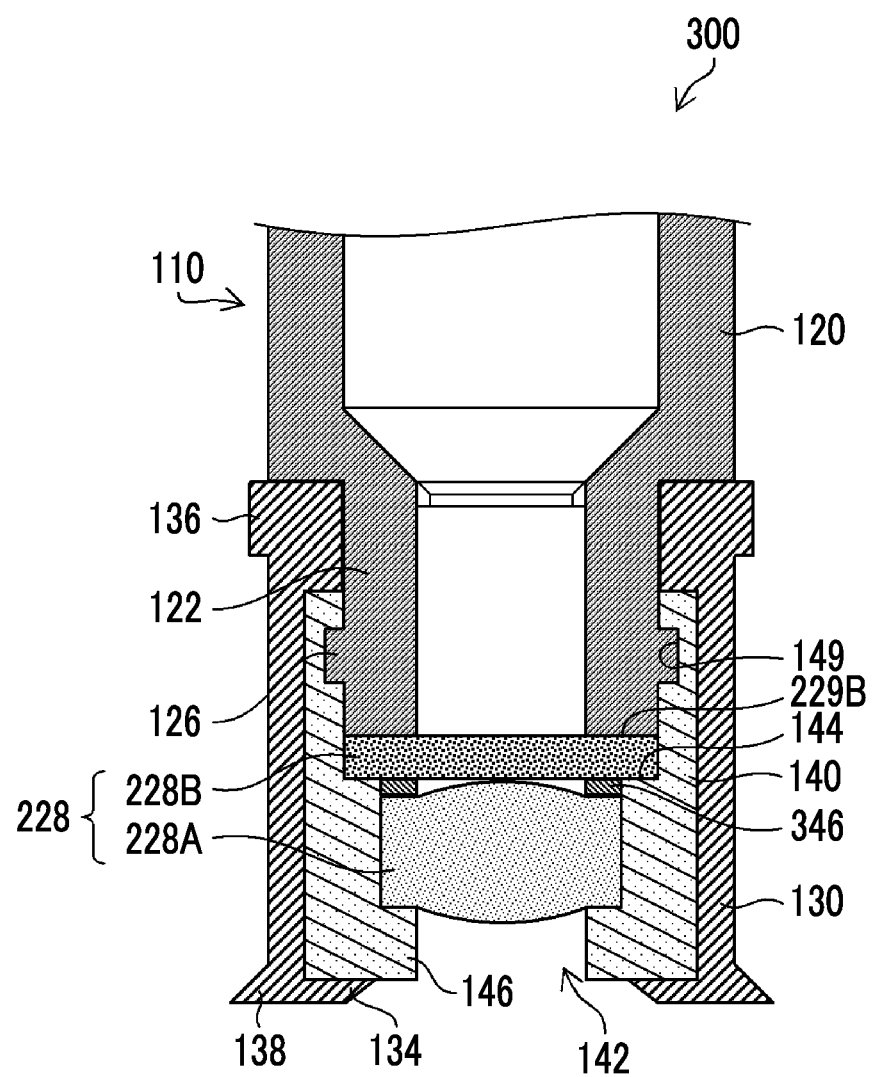
FIG. 9 is an enlarged view of still another embodiment of the tip part of the holding instrument.

FIG. 7 to FIG. 9 are enlarged views illustrating other configurations of the filter and the sealing member provided at the tip of the holding instrument.

In the holding instrument 200 illustrated in FIG. 7, a filter 228 is composed of two filters and has a first filter 228A which is a depth filter and a second filter 228B which is a membrane filter, in order from the inflow port 142 side. Since the filter 228 has two filters which are the depth filter and the membrane filter, a blood cell component can be reliably captured by the membrane filter even in a case where the blood cell component passes through the depth filter. In a case where the filter 128 described in FIG. 2 to FIG. 6 is composed of one filter, a depth filter can be used. In FIG. 7 as well, the first filter 228A is composed of one depth filter; however, it may be composed of two or more depth filters.

In the holding instrument 200 illustrated in FIG. 7, the first filter 228A and the second filter 228B are arranged to overlap each other, where the filter 228 is held due to being pressed by the protrusion part 146 of the holder 140 and the tip of the reduced diameter part 122.

FIG. 8 is an enlarged view illustrating still another embodiment of the tip part of the holding instrument. In the holding instrument 250 illustrated in FIG. 8, the first filter 228A and the second filter 228B are arranged to overlap each other, where the filter 228 is held due to being pressed by the protrusion part 146 of the holder 140 and the tip of the reduced diameter part 122. In the holding instrument 250 illustrated in FIG. 8, the second filter 228B has a larger area than the first filter 228A. In addition, a protrusion portion 229B protruding from the first filter 228A of the second filter 228B, which does not overlap with the first filter 228A, is pressed by the reduced diameter part 122 and the stepped part 144 of the holder 140, whereby the second filter 228B is held. With such a configuration, the end part of the second filter 228B can be reliably compressed and held. As a result, it is possible to prevent the intrusion of the blood, which prevents hemolysis.

FIG. 9 is an enlarged view of still another embodiment of the tip part of the holding instrument. The holding instrument 300 illustrated in FIG. 9 differs from the holding instrument 250 illustrated in FIG. 8 in that a spacer 346 is provided between the first filter 228A and the second filter 228B. As illustrated in FIG. 9, since the spacer 346 is provided, first, the second filter 228B is pressed and held by the reduced diameter part 122 of the cylinder 110 and the stepped part 144 of the holder 140 in the same manner as in FIG. 8. In addition, the first filter 228A is pressed by the reduced diameter part 122 and the protrusion part 146 of the holder 140 and is held through the second filter 228B and the spacer 346. Further, the second filter 228B is held by the reduced diameter part 122 and the stepped part 144, and, in addition, is pressed by the reduced diameter part 122 and the protrusion part 146 to be held through the first filter 228A and the spacer 346. Since the spacer 346 is provided between the first filter 228A and the second filter 228B, the first filter 228A can be pressed by the first protrusion part 134 and the spacer 346. Further, the second filter 228B can be pressed by the reduced diameter part 122 and the spacer 346. As a result, the first filter 228A and the second filter 228B can be reliably held.

Since the end part of the filter is reliably held by being compressed, it is possible to prevent the blood collected in the blood collection container 10 from not passing through the filter and from intruding between the filter and the sealing member. As a result, blood separation can be reliably carried out, and hemolysis can be prevented.

Figure 10:
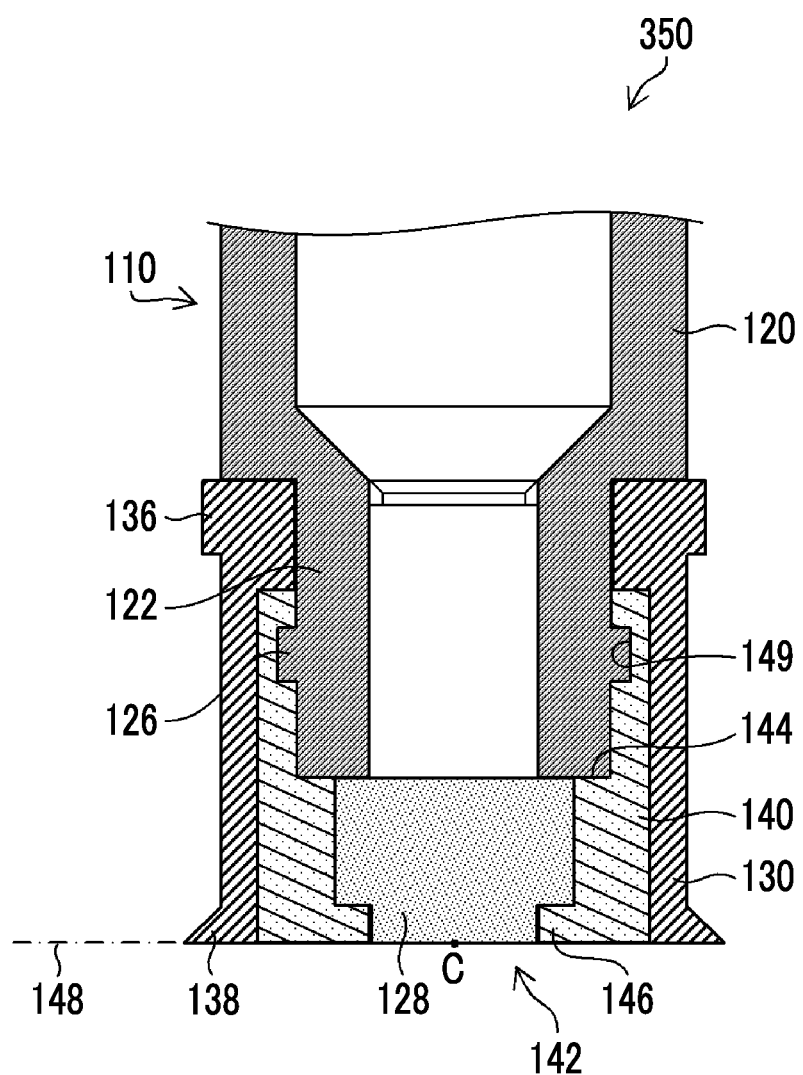
FIG. 10 is an enlarged view of still another embodiment of the tip part of the holding instrument.
Figure 11:
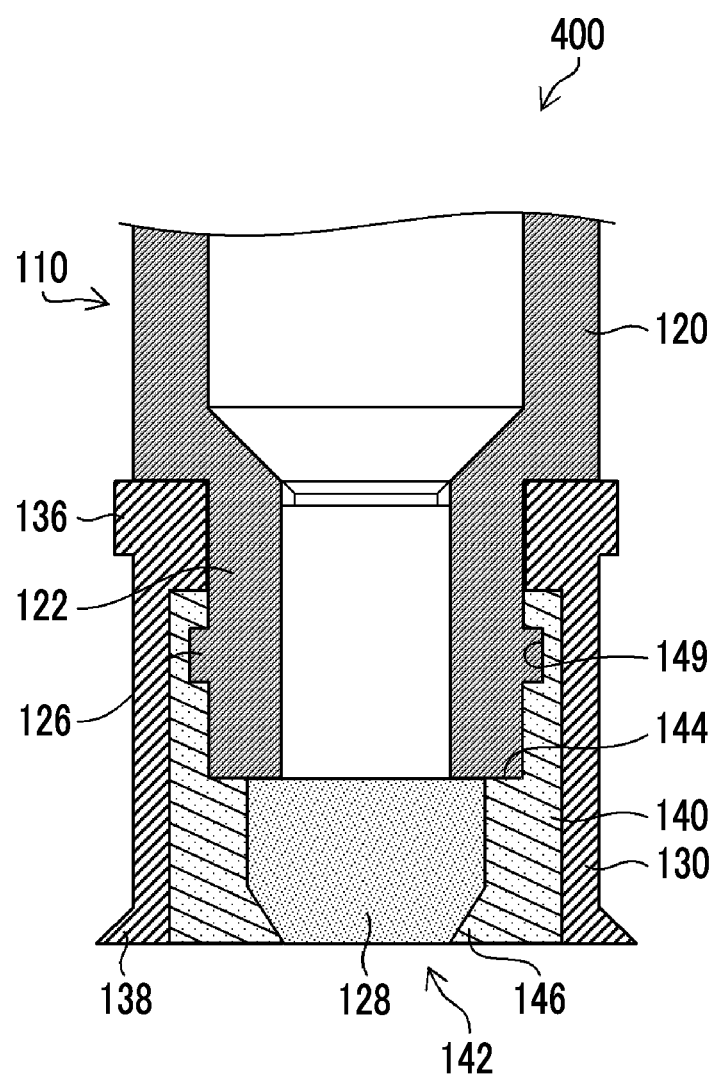
FIG. 11 is an enlarged view of still another embodiment of the tip part of the holding instrument.
Figure 12:
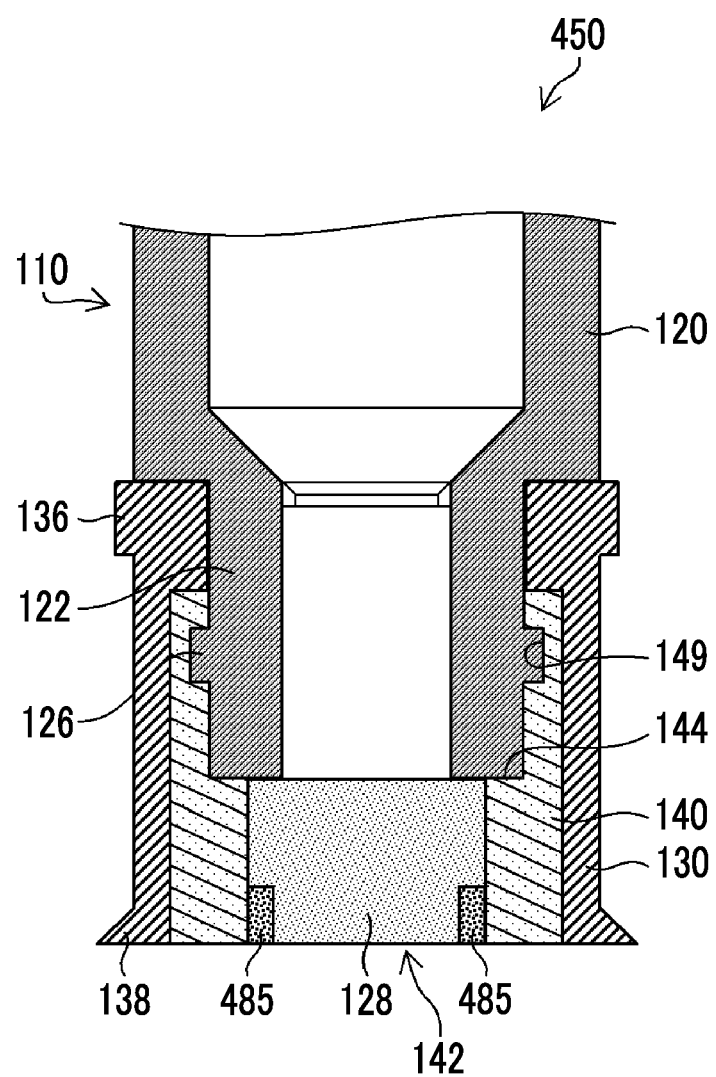
FIG. 12 is an enlarged view of still another embodiment of the tip part of the holding instrument.

FIG. 10 to FIG. 12 are enlarged views of still another embodiment of the tip part of the holding instrument. In the embodiments illustrated in FIG. 6 to FIG. 9, the filter is held by being pressed by the sealing member and the reduced diameter part of the cylinder; however, the aspect of holding the filter is not limited to this. In a holding instrument 350 illustrated in FIG. 10, the filter 128 is held by being pressed in the lateral direction (in the side direction) by the L-shaped protrusion part 146 of the holder 140. In addition to providing an L-shaped protrusion part as illustrated in FIG. 10, in a case of being compressed in the lateral direction, the filter 128 can be held by being compressed in the lateral direction, by being inclined to narrow the tip side so that the protrusion part 146 expands toward the tip side of the protrusion part 146 as in a holding instrument 400 illustrated in FIG. 11.

Further, as in a holding instrument 450 illustrated in FIG. 12, the holder 140 and the filter 128 may be fixed by an adhesive 485. As the material used as the adhesive 485, it is preferable to use a material that does not hydrophobize the filter.

In the holding instruments illustrated in FIG. 10 to FIG. 12, the filter 128 is pressed in the lateral direction, and the filter 128 is in contact with the tip side end part 146A of the inflow port 142, which is formed by the protrusion part 146 of the holder 140. In this case, as illustrated in FIG. 10, the imaginary line 148 is drawn along the tip (the lower end) of the holder 140. In such a case as well, in a case where the position of the sealing member is set to be on a side opposite to the direction of insertion of the holding instrument from the imaginary line 148, that is, on the upper side of the imaginary line 148, the holder 140 can be interposed between the sealing member 130 and the filter 128. As a result, the siloxane generated from the sealing member 130 can be made to be difficult to reach the filter 128, and thus the filter can be prevented from becoming hydrophobized.

Further, since the filter is pressed in the lateral direction or the filter is held by an adhesive, the end part of the filter is not compressed. However, in a case where the holder is interposed between the filter and the sealing member, the siloxane generated from the sealing member can be prevented from being reaching the filter. As a result, the filter can be prevented from being hydrophobized.

As described above, according to the present embodiment, since the intermediate member is arranged between the filter for filtering a predetermined component (plasma or serum) in blood and the sealing member for maintaining the liquid tightness and the smoothness between the first container and the second container, the siloxane generated from the sealing member can be prevented from being reaching the filter. As a result, the filter can be prevented from being hydrophobized.

EXPLANATION OF REFERENCES

1: accommodation instrument
10: blood collection container
12: screw part
14: locking part
16: bottom part
18: leg part
20: slit groove
22: diluent
24: cap
26: packing
100, 200, 250, 300, 350, 400, 450: holding instrument
110: cylinder
112: cap
114: sealing member
116: expanded diameter part
118: thin-wall portion
120: body part
122: reduced diameter part
124: locking protrusion part
126: outer flange part
128, 228: filter
130: sealing member
134: first protrusion part
136: second protrusion part
138: third protrusion part
140: holder
142: inflow port
144: stepped part
146: protrusion part
146A: tip side end part
148: imaginary line
149: groove
152: grip part
154: mandrel part
156: space
158: lower end part
160: stepped part
162: upper end part
164: apex part
228A: first filter
228B: second filter
229B: overhang part
346: spacer
485: adhesive

What is claimed is:

1. A biological specimen separation instrument comprising:
a first container that accommodates a collected biological specimen;
a filter for filtering a predetermined component in the collected biological specimen; and
a second container that accommodates the predetermined component filtered by the filter, the second container being configured to be inserted into the first container,
wherein a sealing member is provided in an outer circumference of the second container on a tip side in a direction of insertion into the first container to be movable in the first container, in a state of being in liquid-tight contact with an interior wall of the first container,
the filter is held in the second container by an intermediate member which is provided between the filter and the sealing member and which forms a biological specimen inflow port to the filter, the intermediate member includes a protrusion part which is in contact with the filter and extends toward a center of the filter, the sealing member includes a sealing protrusion part which is in contact with the intermediate member and extends toward the center of the filter, the filter is held by being pressed between the intermediate member and the second container.

2. The biological specimen separation instrument according to claim 1,
wherein the filter is a hydrophilic filter.

3. The biological specimen separation instrument according to claim 1,
wherein a Shore A hardness of the sealing member is 20 or more and 90 or less.

4. The biological specimen separation instrument according to claim 1,
wherein a Shore D hardness of the intermediate member is 20 or more.

5. The biological specimen separation instrument according claim 1,
wherein a material of the intermediate member is a resin.

6. The biological specimen separation instrument according to claim 5,
wherein the resin is selected from polyvinyl chloride, polyethylene, polypropylene, polystyrene, acrylonitrile-butadiene-styrene, acrylonitrile-styrene, polymethylmethacrylate, polyethylene terephthalate, polyamide, polyacetal, polycarbonate, a polyphenyl ether, polybutylene terephthalate, and polyvinylidene fluoride.

7. The biological specimen separation instrument according to claim 1,
wherein a contact angle of the intermediate member is larger than a contact angle of the filter.

8. The biological specimen separation instrument according to claim 7,
wherein the contact angle of the filter is 500 or less.

9. The biological specimen separation instrument according to claim 1,
wherein the filter has a first filter which is a depth filter and a second filter which is a membrane filter, and
the first filter and the second filter are held by being pressed by the intermediate member and the second container.

10. The biological specimen separation instrument according to claim 9,
wherein a surface of the second filter on which the second filter is in contact with the first filter has a larger area than a surface of the first filter on which the first filter is in contact with the second filter, and
the first filter and the second filter are overlapped to be held by being pressed between the intermediate member and the second container, and a protrusion portion of the second filter, which does not overlap with the first filter, is held by being pressed between the intermediate member and the second container.

11. The biological specimen separation instrument according to claim 10
wherein a spacer is provided between the first filter and the second filter.

* * * * *